United States Patent
Hassen

(12) 
(10) Patent No.: US 6,485,741 B2
(45) Date of Patent: Nov. 26, 2002

(54) GRANULATE WITH HIGH CONTENT OF L-CARNITINE OR AN ALKANOYL L-CARNITINE

(75) Inventor: Ken Hassen, Malvern, PA (US)

(73) Assignee: Biosint S.p.A., Rome (IT)

( * ) Notice: Subject to any disclaimer, the term of this patent is extended or adjusted under 35 U.S.C. 154(b) by 0 days.

(21) Appl. No.: 09/962,605

(22) Filed: Sep. 26, 2001

(65) Prior Publication Data

US 2002/0025984 A1 Feb. 28, 2002

Related U.S. Application Data

(63) Continuation of application No. PCT/IT00/00097, filed on Mar. 22, 2000.

(30) Foreign Application Priority Data

Mar. 26, 1999 (IT) ........................................ RM99A0189

(51) Int. Cl.⁷ ............................ A61K 9/48; A61K 9/14; A61K 9/54; A61K 9/20; A61K 9/50
(52) U.S. Cl. ........................ 424/451; 424/489; 424/458; 424/464; 424/465; 424/499; 424/501
(58) Field of Search ............................... 424/489, 451, 424/458, 464, 465, 499, 501

(56) References Cited

U.S. PATENT DOCUMENTS 5,576,348 A * 11/1996 Kuratsune et al.
5,741,524 A * 4/1998 Staniforth et al.
5,753,703 A * 5/1998 Cavazza et al.
6,051,253 A * 4/2000 Zettler et al.

FOREIGN PATENT DOCUMENTS

| EP | 0 206 240 | 12/1986 |
| EP | 0 207 011 | 12/1986 |
| EP | 0 434 088 | 6/1991 |
| GB | 2 052 976 | 2/1981 |
| JP | 3-120211 | 5/1991 |

OTHER PUBLICATIONS

Database WPI, Section Ch, Week 199127 Derwent Publications Ltd., London, GB; Class A96, AN 1991–196392—XP 002150435.

* cited by examiner

Primary Examiner—Thurman K. Page
Assistant Examiner—Simon J. Oh
(74) Attorney, Agent, or Firm—Nixon & Vanderhye P.C.

(57) ABSTRACT

A granulate is described containing granules of an active ingredient endowed with therapeutic/nutritional activity coated with a granulating/bonding agent, suitable for conversion into a solid administration form with a very high content of active ingredient, particularly in the form of tablets obtained by means of a direct compression procedure, or suitable for constituting the content of capsules.

11 Claims, No Drawings

GRANULATE WITH HIGH CONTENT OF L-CARNITINE OR AN ALKANOYL L-CARNITINE

This is a continuation of application No. PCT/IT00/00097, filed Mar. 22, 2000.

The invention described herein relates to a granulated product containing granules of an active ingredient endowed with therapeutic/nutritional activity, coated with a pharmacologically acceptable granulating/bonding agent, said granulate being suitable for conversion into solid administration forms with a very high content of active ingredient, particularly in the form of tablets by means of a direct compression procedure, or for constituting the content of capsules. The invention also relates to the solid administration forms, particularly tablets and granules, obtained from said granulated product.

In the description which follows here below, as in the claims, what is meant by "granulate" is not only an actual granulate as such but also powders, crystalline aggregates, pellets and microcapsules. As regards the microcapsules in particular, numerous procedures are known for their preparation. The reader is referred, for example, to the publications "Microcapsules and Microencapsulation Techniques" (1976) and to "Microcapsules and other Capsules. Advances since 1975" (1979), both by M. H. Guttcho; "Microencapsulation" by J. R. Nixon and "Microencapsulation and Related Process" by P. B. Deasy (Volume 3 of the series Drugs and Pharmaceutical Sciences) and to U.S. Pat. Nos. 3,155,590, 3,196,827, 3,253,944, 3,341,416 and 3,415,758.

The active ingredient endowed with therapeutic/nutritional activity from which we are interested in obtaining tablets with a high active ingredient content by means of a direct compression procedure or capsules is L-carnitine inner salt or an alkanoyl L-carnitine inner salt in which the straight- or branched-chain alkanoyl has 2–6 carbon atoms, or one of their pharmacologically acceptable salts.

Though the invention applies to all the "carnitines" as defined above, hereinafter, for the sake of simplicity, reference will be made only to L-carnitine inner salt, and likewise, again for the sake of simplicity, reference will be made to the preparation of a granulate, in that the operational modifications for the preparation, for instance, of a microencapsulated product will be obvious to any normal expert, also on the basis of the references in the literature and the patents mentioned above.

It has been known for some time now that carnitine lends itself to various therapeutic uses. For example, L-carnitine is used in the cardiovascular field as a support drug in the treatment of acute and chronic myocardial ischaemia, angina pectoris, heart failure and arrhythmias (U.S. Pat. Nos. 4,649,159 and 4,656,191, Sigma-Tau). In nephrology, it is administered to chronic uraemic patients undergoing regular haemodialysis treatment to counteract muscular asthenia and the onset of cramps (U.S. Pat. No. 4,272,549, Sigma-Tau). It is also effective for the treatment of chronic obliterating arteriopathy, particularly in patients presenting the symptoms of intermittent claudication in a severely disabling form (U.S. Pat. No. 4,968,719, Sigma-Tau). Moreover, the use of L-carnitine for applications other than purely therapeutic (or "ethical") applications, albeit akin to the latter, in the field of health food supplements and the so-called "neutraceuticals" is rapidly spreading.

This result stems from the increasingly widespread and scientifically supported recognition that, in athletes or in subjects practising sport even at non-professional level, L-carnitine contributes markedly towards supplying the skeletal muscles with energy and towards increasing resistance to prolonged, intense physical stress, thereby enhancing the performance of such subjects.

In addition, L-carnitine constitutes an indispensable nutritional supplement for vegetarians whose diet has a low carnitine content and a low content of the two naturally occurring amino acids, lysine and methionine, which are the precursors of L-carnitine biosynthesis in the kidneys and liver. The same considerations hold good for those subjects who find themselves obliged to go on low-protein diets for more or less prolonged periods. In view of the known hygroscopicity and instability of L-carnitine, it is surprising that L-carnitine inner salt can be formulated in a granulate with a high L-carnitine content (>94% by weight) which lends itself to conversion into tablets by means of a direct compression procedure or to constituting the content of capsules. It is well known, in fact, that the high degree of hygroscopicity of L-carnitine inner salt gives rise to complex problems of processing, stability and storability both of the raw materials and the finished products. For example, tablets of L-carnitine inner salt have to be packaged in blister packs to keep them away from contact with the air, since, otherwise, even in the presence of normal humidity conditions, they would undergo alterations in a short space of time, becoming swollen, pasty and sticky. Tablets, however, are the preferred administration form, in that they make it particularly simple for users to take the active ingredient and comply with optimal dosage regimens. Similar considerations also apply in the case of capsules.

To date attempts have been made to solve the problem of the hygroscopicity of L-carnitine inner salt which is perceived as being particularly important in the production of solid administration forms, and most notably, tablets, by converting L-carnitine to salts with pharmacologically acceptable acids on the basis of the assumption that such salts maintain the same therapeutic/nutritional activities as the inner salt, and providing no unwanted toxic or side effects occur.

This desirable objective is not always fully achieved. Moreover, in the L-carnitine salts the L-carnitine content is generally lower than 60–70%, depending upon the molecular weight of the salifying acid and the carnitine:acid ratio of 2:1 or 1:1 in the salt.

To date, two L-carnitine salts have been developed and marketed which overcome the problem of the hygroscopicity presented by L-carnitine: L-carnitine L-tartrate and acid fumarate.

Though L-carnitine tartrate presents a greater percentage of carnitine than acid fumarate (68% as against 58%), the tartrate may cause troublesome gastrointestinal disorders due to the presence of tartaric acid in the salt, which is known for its use as a laxative.

The advantages which would result from the production of solid administration forms, and particularly tablets, without necessarily having first to convert the L-carnitine inner salt to a different pharmacologically acceptable salt, or at any rate to a salt which presents unpleasant side effects, such as those of tartrate, are therefore obvious. Equally well known are the advantages of both an operational and economic nature which the process of direct compression presents in the preparation of tablets as compared to traditional methods involving the pretreatment (wet and dry granulation) of the starting material (in this connection, see, for example: Jarrar A. Khan et al., The production of tablets by direct compression, Canadian J. Pharm. Sci., Vol. 8, n. 1, 1–5, 1973).

It has now been found that the above-mentioned problems are solved by the granulated product according to the invention described herein, containing granules of an active ingredient endowed with therapeutic/nutritional activity and a pharmacologically acceptable granulating/bonding material for said granules, the granulated product being suitable for conversion into solid administration forms, particularly tablets, by means of a direct compression procedure or for constituting the content of capsules, which is characterised in that it contains:

(a) from 92 to 96% by weight, calculated in relation to the weight of the granulated product, of an active ingredient selected from the group consisting of L-carnitine inner salt, an alkanoyl L-carnitine inner salt, in which the straight- or branched-chain alkanoyl group has 2–6 carbon atoms, or one of their pharmacologically acceptable salts, and (b) from 4 to 8% by weight, calculated in relation to the weight of the granulated product, of a granulating/bonding material selected from the group consisting of polyvinylpyrrolidone, hydroxyethylcellulose, hydroxypropylcellulose, hydroxypropyl-methylcellulose, hydroxybutylcellulose, polyethyleneglycol, microcrystalline cellulose, cellulose acetate phthalate, methylcellulose, ethylcellulose, polyvinylalcohol, and sytrene maleic anhydride, or mixtures of these.

According to an alternative formula, the product according to the invention may additionally contain:

(c) from 0.1 to 1% of amorphous silica granulate by weight, calculated in relation to the weight of the granulated product.

Also included within the framework of the invention described herein are tablets obtained by means of direct compression of said granulated product and capsules containing the granulated product, the preparation techniques for which are well known to experts in pharmaceutical technology.

According to a particularly preferred form of execution for the L-carnitine inner salt, the granulated product contains:

(a) from 94 to 96% of L-carnitine inner salt by weight, calculated in relation to the weight of the granulated product; and (b) from 4 to 6% of polyvinylpyrrolidone by weight, calculated in relation to the weight of the granulated product, to which may possibly be added:

(c) from 0.4 to 0.6% of amorphous silica by weight, calculated in relation to the weight of the granulated product According to a preferred form of execution for the alkanoyl L-carnitines, the alkanoyl L-carnitine inner salt is selected from the group consisting of acetyl L-carnitine inner salt, propionyl L-carnitine inner salt and isovaleryl L-carnitine inner salt, while the pharmacologically acceptable salt of L-carnitine or alkanoyl L-carnitine is preferably selected from the group consisting of fumarate, tartrate or chloride. Particularly preferred is acetyl L-carnitine chloride.

EXAMPLE 1

Preparation of a Granulated Product Containing Approximately 94% by Weight of L-carnitine Inner Salt A granulating solution was prepared by placing 37.5 kg of demineralised water in a stainless steel container equipped with a stirrer, into which 7.5 kg of polyvinylpyrrolidone, PVPK30, were then poured under moderate sting.

141.75 of L-carnitine inner salt, obtained by sieving with a 1,250 mm sieve mounted on an Alexanderwerk granulator, were directly fed into the drum of an Aeromatic fluid-bed granulator (Aeromatic Inc., Towaco, N.J. 07082-USA.

After preheating the L-carnitine inner salt at 60–65° C., the granulation was done in the fluid-bed granulator at a spray rate of 750 g/minute. The total spray time was 60 minutes. The water content (determined using the Karl Fisher method) at the end of spraying was approximately 3% by weight.

The product obtained was dried at 60–70° C. until a product was obtained with humidity (determined with the Karl Fisher method) less than 1.5% by weight.

The product was then dry-sieved using a 1,250 mm sieve on an Alexanderwerk granulator to select granules of the size desired.

EXAMPLE 2

Preparation of a Granulated Product Containing Approximately 94% of L-carnitine Inner Salt by Weight The procedure outlined in Example 1 was repeated. However, before the final sieving, to the fluid-bed granulator drum containing the product at humidity below 1.5% by weight were added 750 g (corresponding to approximately 0.5% by weight) of amorphous silica (Syloid 244) and the resulting mixture was blended in the fluid bed for approximately 5 minutes.

Final sieving was then performed, as described in Example 1.

EXAMPLE 3

Preparation of Tablets by Direct Compression

The granulates in Examples 1 and 2 were transformed into tablets by means of a routine direct compression procedure (see the above cited article by Khan et al. and Remington's Pharmaceutical Sciences, 17th Ed. (1985), pp. 1613–1614).

The tablets thus obtained presented excellent stability properties and remain unaltered over time.

EXAMPLE 4

Preparation of Capsules

Hard gelatine capsules were prepared, the content of which consisted of the granulate in Examples 1 and 2, respectively.

These capsules presented no sign of alteration after storage for two months in a thermostat at 35° C.

What is claimed is:

1. A granulated product containing granules of an active ingredient endowed with therapeutic/nutritional activity and a pharmacologically acceptable granulating/bonding agent, said granulated product being suitable for conversion into solid administration forms by means of a direct compression procedure, or for constituting the content of capsules, wherein said product consists of:

(a) from 92 to 96% by weight, calculated in relation to the weight of the granulated product, of an active ingredient selected from the group consisting of L-carnitine inner salt, an alkanoyl L-carnitine inner salt, in which the straight- or branched-chain alkanoyl group has 2–6 carbon atoms, or one of their pharmacologically acceptable salts; and (b) from 4 to 8% by weight, calculated in relation to the weight of the granulated product, of a granulating/bonding material selected from the group consisting of polyvinylpyrrolidone, hydroxyethylcellulose, hydroxypropylcellulose, hydroxypropylmethylcellulose, hydroxybutylcellulose, polyethyleneglycol, microcrystalline cellulose, cellulose acetate phthalate, methylcellulose, ethylcellulose, polyvinylalcohol, styrene maleic anhydride, and mixtures thereof.

2. A granulated product containing granules of an active ingredient endowed with therapeutic/nutritional activity and a pharmacologically acceptable granulating/bonding agent, said granulated product being suitable for conversion into solid administration forms by means of a direct compression procedure, or for constituting the content of capsules, wherein said product consists of:

(a) from 92 to 96% by weight, calculated in relation to the weight of the granulated product, of an active ingredient selected from the group consisting of L-carnitine inner salt, an alkanoyl L-carnitine inner salt, in which the straight- or branched-chain alkanoyl group has 2–6 carbon atoms, or one of their pharmacologically acceptable salts;

(b) from 4 to 8% by weight, calculated in relation to the weight of the granulated product, of a granulating/bonding material selected from the group consisting of polyvinylpyrrolidone, hydroxyethylcellulose, hydroxypropylcellulose, hydroxypropylmethylcellulose, hydroxybutylcellulose, polyethyleneglycol, microcrystalline cellulose, cellulose acetate phthalate, methylcellulose, ethylcellulose, polyvinylalcohol, styrene maleic anhydride, and mixtures thereof; and (c) from 0.1 to 1% of amorphous silica by weight, calculated in relation to the weight of the granulated product.

3. A tablet obtained by direct compression of the granulated product according to claim 1 or 2.

4. A capsule containing the granulated product according to claim 1 or 2.

5. A granulated product according to claim 1 or 2 consisting of:

(a) from 94 to 96% of L-carnitine inner salt by weight, calculated in relation to the weight of the granulated product; and (b) from 4 to 6% of polyvinylpyrrolidone by weight, calculated in relation to the weight of the granulated product.

6. A granulated product according to claim 1 or 2 consisting of:

(a) from 94 to 96% of L-carnitine inner salt by weight, calculated in relation to the weight of the granulated product;

(b) from 4 to 6% of polyvinylpyrrolidone by weight, calculated in relation to the weight of the granulated product; and (c) from 0.4 to 0.6% of amorphous silica granulate by weight, calculated in relation to the weight of the granulated product.

7. A granulated product according to claim 1 or 2, in which the alkanoyl L-carnitine inner salt is selected from the group consisting of acetyl L-carnitine inner salt, propionyl L-carnitine inner salt and isovaleryl L-carnitine inner salt.

8. A granulated product according to claim 1 or 2, in which the pharmacologically acceptable salt of L-carnitine or of the alkanoyl L-carnitine is selected from the group consisting of their fumarates, tartrates and chlorides.

9. A granulated product according to claim 1 or 2, in which the active ingredient contains acetyl L-carnitine chloride.

10. A tablet obtained by direct compression of the granulated product according to claim 7.

11. A capsule containing the granulated product according to claim 7.

* * * * *